(12) United States Patent
Martinelli et al.

(10) Patent No.: US 8,057,407 B2
(45) Date of Patent: Nov. 15, 2011

(54) SURGICAL SENSOR

(75) Inventors: Michael A Martinelli, Winchester, MA (US); Mark W Hunter, Broomfield, CO (US); Sheri McCoid, Broomfield, CO (US); Paul Kessman, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1772 days.

(21) Appl. No.: 11/247,848

(22) Filed: Oct. 11, 2005

(65) Prior Publication Data

US 2006/0036189 A1    Feb. 16, 2006

Related U.S. Application Data

(63) Continuation of application No. 10/289,869, filed on Nov. 7, 2002, now Pat. No. 7,007,699, which is a continuation of application No. 09/428,721, filed on Oct. 28, 1999, now Pat. No. 6,499,488.

(51) Int. Cl.
  *A61B 5/103* (2006.01)
(52) U.S. Cl. ........ 600/595; 600/407; 600/437; 600/438; 600/439; 600/440; 600/441; 600/442; 600/443; 600/444; 600/461; 600/567; 600/587
(58) Field of Classification Search .................. 600/407, 600/437–444, 461, 567, 587; 606/1; 702/153
See application file for complete search history.

(56) References Cited

U.S. PATENT DOCUMENTS

| | | | |
|---|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,614,950 A | 10/1971 | Rabey |

(Continued)

FOREIGN PATENT DOCUMENTS

CA    964149    3/1975

(Continued)

OTHER PUBLICATIONS

Adams et al., Computer-Assisted Surgery, IEEE Computer Graphics & Applications, pp. 43-51, (May 1990).

(Continued)

*Primary Examiner* — Tse Chen
*Assistant Examiner* — Baisakhi Roy
(74) *Attorney, Agent, or Firm* — Harness, Dickey (57) ABSTRACT

An integrated surgical anchor/localization sensor is disclosed. The anchor is adapted to be secured to an anatomical structure and contains a sensor housing. A receiver is located within the sensor housing and is adapted to sense reference signals generated by a surgical guidance system. A transmitter, connected to the receiver, conveys to a processor signals received by the receiver, so that the signals transmitted by the receiver are indicative of a current position of the anchor. Various other structures and methods are also disclosed.

29 Claims, 4 Drawing Sheets

U.S. PATENT DOCUMENTS

| | | |
|---|---|---|
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,445,106 A | 4/1984 | Shah |
| 4,485,815 A | 12/1984 | Amplatz |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,671,287 A | 6/1987 | Fiddian-Green |
| 4,673,352 A | 6/1987 | Hansen |
| 4,688,037 A | 8/1987 | Krieg |
| 4,701,049 A | 10/1987 | Beckmann et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Öberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |

| Patent | Date | Inventor |
|---|---|---|
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlöndorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndort et al. |
| 5,353,807 A | 10/1994 | DeMarco |
| 5,359,417 A | 10/1994 | Müller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,403,321 A | 4/1995 | DiMarco |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlöndorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-Haim |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,383,454 A | 12/1996 | Bucholz |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |

| | | | | | | |
|---|---|---|---|---|---|---|
| 5,595,193 A | 1/1997 | Walus et al. | 5,803,089 A | 9/1998 | Ferre et al. | |
| 5,596,228 A | 1/1997 | Anderton et al. | 5,807,252 A | 9/1998 | Hassfeld et al. | |
| 5,600,330 A | 2/1997 | Blood | 5,810,008 A | 9/1998 | Dekel et al. | |
| 5,603,318 A | 2/1997 | Heilbrun et al. | 5,810,728 A | 9/1998 | Kuhn | |
| 5,611,025 A | 3/1997 | Lorensen et al. | 5,810,735 A | 9/1998 | Halperin et al. | |
| 5,617,462 A | 4/1997 | Spratt | 5,820,553 A | 10/1998 | Hughes | |
| 5,617,857 A | 4/1997 | Chader et al. | 5,823,192 A | 10/1998 | Kalend et al. | |
| 5,619,261 A | 4/1997 | Anderton | 5,823,958 A | 10/1998 | Truppe | |
| 5,622,169 A | 4/1997 | Golden et al. | 5,828,725 A | 10/1998 | Levinson | |
| 5,622,170 A | 4/1997 | Schulz | 5,828,770 A | 10/1998 | Leis et al. | |
| 5,627,873 A | 5/1997 | Hanover et al. | 5,829,444 A | 11/1998 | Ferre et al. | |
| 5,628,315 A | 5/1997 | Vilsmeier et al. | 5,831,260 A | 11/1998 | Hansen | |
| 5,630,431 A | 5/1997 | Taylor | 5,833,608 A | 11/1998 | Acker | |
| 5,632,432 A | 5/1997 | Schulze et al. | 5,834,759 A | 11/1998 | Glossop | |
| 5,636,644 A | 6/1997 | Hart et al. | 5,836,954 A | 11/1998 | Heilbrun et al. | |
| 5,638,819 A | 6/1997 | Manwaring et al. | 5,840,024 A | 11/1998 | Taniguchi et al. | |
| 5,640,170 A | 6/1997 | Anderson | 5,840,025 A | 11/1998 | Ben-Haim | |
| 5,642,395 A | 6/1997 | Anderton et al. | 5,843,076 A | 12/1998 | Webster, Jr. et al. | |
| 5,643,268 A | 7/1997 | Vilsmeier et al. | 5,848,967 A | 12/1998 | Cosman | |
| 5,645,065 A | 7/1997 | Shapiro et al. | 5,851,183 A | 12/1998 | Bucholz | |
| 5,646,524 A | 7/1997 | Gilboa | 5,865,846 A | 2/1999 | Bryan et al. | |
| 5,647,361 A | 7/1997 | Damadian | 5,868,674 A | 2/1999 | Glowinski et al. | |
| 5,662,111 A | 9/1997 | Cosman | 5,868,675 A | 2/1999 | Henrion et al. | |
| 5,664,001 A | 9/1997 | Tachibana et al. | 5,868,789 A | 2/1999 | Huebner | |
| 5,674,296 A | 10/1997 | Bryan et al. | 5,871,445 A | 2/1999 | Bucholz | |
| 5,676,673 A | 10/1997 | Ferre et al. | 5,871,455 A | 2/1999 | Ueno | |
| 5,681,260 A | 10/1997 | Ueda et al. | 5,871,487 A | 2/1999 | Warner et al. | |
| 5,682,886 A | 11/1997 | Delp et al. | 5,873,822 A | 2/1999 | Ferre et al. | |
| 5,682,890 A | 11/1997 | Kormos et al. | 5,882,304 A | 3/1999 | Ehnholm et al. | |
| 5,690,108 A | 11/1997 | Chakeres | 5,884,410 A | 3/1999 | Prinz | |
| 5,694,945 A | 12/1997 | Ben-Haim | 5,889,834 A | 3/1999 | Vilsmeier et al. | |
| 5,695,500 A | 12/1997 | Taylor et al. | 5,891,034 A | 4/1999 | Bucholz | |
| 5,695,501 A | 12/1997 | Carol et al. | 5,891,157 A | 4/1999 | Day et al. | |
| 5,697,377 A | 12/1997 | Wittkampf | 5,904,691 A | 5/1999 | Barnett et al. | |
| 5,702,406 A | 12/1997 | Vilsmeier et al. | 5,907,395 A | 5/1999 | Schulz et al. | |
| 5,711,299 A | 1/1998 | Manwaring et al. | 5,913,820 A | 6/1999 | Bladen et al. | |
| 5,713,946 A | 2/1998 | Ben-Haim | 5,920,395 A | 7/1999 | Schulz | |
| 5,715,822 A | 2/1998 | Watkins | 5,921,992 A | 7/1999 | Costales et al. | |
| 5,715,836 A | 2/1998 | Kliegis et al. | 5,923,727 A | 7/1999 | Navab | |
| 5,718,241 A | 2/1998 | Ben-Haim et al. | 5,928,248 A | 7/1999 | Acker | |
| 5,727,552 A | 3/1998 | Ryan | 5,930,741 A * | 7/1999 | Kramer | 702/153 |
| 5,727,553 A | 3/1998 | Saad | 5,938,603 A | 8/1999 | Ponzi | |
| 5,729,129 A | 3/1998 | Acker | 5,938,694 A | 8/1999 | Jaraczewski et al. | |
| 5,730,129 A | 3/1998 | Darrow et al. | 5,947,980 A | 9/1999 | Jensen et al. | |
| 5,730,130 A | 3/1998 | Fitzpatrick et al. | 5,947,981 A | 9/1999 | Cosman | |
| 5,732,703 A | 3/1998 | Kalfas et al. | 5,950,629 A | 9/1999 | Taylor et al. | |
| 5,735,278 A | 4/1998 | Hoult et al. | 5,951,475 A | 9/1999 | Gueziec et al. | |
| 5,738,096 A | 4/1998 | Ben-Haim | 5,951,571 A | 9/1999 | Audette | |
| 5,740,802 A | 4/1998 | Nafis et al. | 5,954,647 A | 9/1999 | Bova et al. | |
| 5,740,808 A | 4/1998 | Panescu et al. | 5,957,844 A | 9/1999 | Dekel et al. | |
| 5,741,214 A | 4/1998 | Ouchi et al. | 5,964,796 A | 10/1999 | Imran | |
| 5,742,394 A | 4/1998 | Hansen | 5,967,980 A | 10/1999 | Ferre et al. | |
| 5,744,953 A | 4/1998 | Hansen | 5,967,982 A | 10/1999 | Barnett | |
| 5,748,767 A | 5/1998 | Raab | 5,968,047 A | 10/1999 | Reed | |
| 5,749,362 A | 5/1998 | Funda et al. | 5,971,997 A | 10/1999 | Guthrie et al. | |
| 5,749,835 A | 5/1998 | Glantz | 5,976,156 A | 11/1999 | Taylor et al. | |
| 5,752,513 A | 5/1998 | Acker et al. | 5,980,535 A | 11/1999 | Barnett et al. | |
| 5,755,725 A | 5/1998 | Druais | 5,983,126 A | 11/1999 | Wittkampf | |
| RE35,816 E | 6/1998 | Schulz | 5,987,349 A | 11/1999 | Schulz | |
| 5,758,667 A | 6/1998 | Slettenmark | 5,987,960 A | 11/1999 | Messner et al. | |
| 5,762,064 A | 6/1998 | Polvani | 5,999,837 A | 12/1999 | Messner et al. | |
| 5,767,669 A | 6/1998 | Hansen et al. | 5,999,840 A | 12/1999 | Grimson et al. | |
| 5,767,960 A | 6/1998 | Orman | 6,001,130 A | 12/1999 | Bryan et al. | |
| 5,769,789 A | 6/1998 | Wang et al. | 6,002,378 A | 12/1999 | Harada et al. | |
| 5,769,843 A | 6/1998 | Abela et al. | 6,006,126 A | 12/1999 | Cosman | |
| 5,769,861 A | 6/1998 | Vilsmeier | 6,006,127 A | 12/1999 | Van Der Brug et al. | |
| 5,772,594 A | 6/1998 | Barrick | 6,011,987 A | 1/2000 | Barnett | |
| 5,775,322 A | 7/1998 | Silverstein et al. | 6,013,087 A | 1/2000 | Adams et al. | |
| 5,776,064 A | 7/1998 | Kalfas et al. | 6,014,580 A | 1/2000 | Blume et al. | |
| 5,782,765 A | 7/1998 | Jonkman | 6,016,439 A | 1/2000 | Acker | |
| 5,787,886 A | 8/1998 | Kelly et al. | 6,019,725 A | 2/2000 | Vesely et al. | |
| 5,792,055 A | 8/1998 | McKinnon | 6,021,343 A | 2/2000 | Foley et al. | |
| 5,795,294 A | 8/1998 | Luber et al. | 6,024,695 A | 2/2000 | Taylor et al. | |
| 5,797,849 A | 8/1998 | Vesely et al. | 6,050,724 A | 4/2000 | Schmitz et al. | |
| 5,799,055 A | 8/1998 | Peshkin et al. | 6,059,718 A | 5/2000 | Taniguchi et al. | |
| 5,799,099 A | 8/1998 | Wang et al. | 6,063,022 A | 5/2000 | Ben-Haim | |
| 5,800,352 A | 9/1998 | Ferre et al. | 6,063,031 A * | 5/2000 | Cundari et al. | 600/439 |
| 5,800,535 A | 9/1998 | Howard, III | 6,071,288 A | 6/2000 | Carol et al. | |
| 5,802,719 A | 9/1998 | O'Farrell, Jr. et al. | 6,073,043 A | 6/2000 | Schneider | |

| | | | | | | |
|---|---|---|---|---|---|---|
| 6,076,008 | A | 6/2000 | Bucholz | 2004/0024309 A1 | 2/2004 | Ferre et al. |
| 6,096,050 | A | 8/2000 | Audette | 2004/0097805 A1 | 5/2004 | Verard et al. |
| 6,104,944 | A | 8/2000 | Martinelli | 2004/0215071 A1 | 10/2004 | Frank et al. |
| 6,106,464 | A | 8/2000 | Bass et al. | 2005/0075632 A1 | 4/2005 | Russell et al. |
| 6,118,845 | A | 9/2000 | Simon et al. | 2005/0085715 A1 | 4/2005 | Dukesherer et al. |
| 6,122,538 | A | 9/2000 | Sliwa, Jr. et al. | 2005/0085720 A1 | 4/2005 | Jascob et al. |
| 6,122,541 | A | 9/2000 | Cosman et al. | 2005/0107882 A1 | 5/2005 | Stone et al. |
| 6,131,396 | A | 10/2000 | Duerr et al. | 2005/0215887 A1 * | 9/2005 | Ben-Haim et al. ............ 600/424 |
| 6,139,183 | A | 10/2000 | Graumann | 2005/0245817 A1 | 11/2005 | Clayton et al. |
| 6,147,480 | A | 11/2000 | Osadchy et al. | 2006/0025677 A1 | 2/2006 | Verard et al. |
| 6,149,592 | A | 11/2000 | Yanof et al. | 2006/0036189 A1 | 2/2006 | Martinelli et al. |
| 6,156,067 | A | 12/2000 | Bryan et al. | 2006/0084867 A1 | 4/2006 | Tremblay et al. |
| 6,161,032 | A | 12/2000 | Acker | 2007/0016006 A1 | 1/2007 | Shachar |
| 6,165,181 | A | 12/2000 | Heilbrun et al. | 2008/0171937 A1 | 7/2008 | Dukesherer et al. |
| 6,167,296 | A | 12/2000 | Shahidi | 2008/0172069 A1 | 7/2008 | Dukesherer et al. |
| 6,172,499 | B1 | 1/2001 | Ashe | 2009/0290771 A1 | 11/2009 | Frank et al. |
| 6,173,199 | B1 | 1/2001 | Gabriel | 2010/0210939 A1 | 8/2010 | Hartmann et al. |
| 6,175,756 | B1 | 1/2001 | Ferre et al. | 2010/0274124 A1 | 10/2010 | Jascob et al. |
| 6,178,345 | B1 | 1/2001 | Vilsmeier et al. | | | |
| 6,194,639 | B1 | 2/2001 | Botella et al. | FOREIGN PATENT DOCUMENTS | | |
| 6,201,387 | B1 | 3/2001 | Govari | DE | 3042343 A1 | 6/1982 |
| 6,203,497 | B1 | 3/2001 | Dekel et al. | DE | 35 08730 | 3/1985 |
| 6,211,666 | B1 | 4/2001 | Acker | DE | 37 17 871 | 5/1987 |
| 6,223,067 | B1 | 4/2001 | Vilsmeier | DE | 38 38011 | 11/1988 |
| 6,226,548 | B1 | 5/2001 | Foley et al. | DE | 38 31 278 A1 | 3/1989 |
| 6,233,476 | B1 | 5/2001 | Strommer et al. | DE | 42 13 426 | 4/1992 |
| 6,236,875 | B1 | 5/2001 | Bucholz et al. | DE | 42 25 112 | 7/1992 |
| 6,246,231 | B1 | 6/2001 | Ashe | DE | 42 33 978 C1 | 4/1994 |
| 6,253,770 | B1 | 7/2001 | Acker et al. | DE | 4233978 | 4/1994 |
| 6,259,942 | B1 | 7/2001 | Westermann et al. | DE | 197 15 202 | 4/1997 |
| 6,273,896 | B1 | 8/2001 | Franck et al. | DE | 197 47 427 | 10/1997 |
| 6,285,902 | B1 | 9/2001 | Kienzle, III et al. | DE | 197 51 761 | 11/1997 |
| 6,298,262 | B1 | 10/2001 | Franck et al. | DE | 19631303 | 2/1998 |
| 6,314,310 | B1 | 11/2001 | Ben-Haim et al. | DE | 198 32 296 | 7/1998 |
| 6,332,089 | B1 | 12/2001 | Acker et al. | DE | 10085137 | 11/2002 |
| 6,341,231 | B1 | 1/2002 | Ferre et al. | DE | 10335388 | 2/2005 |
| 6,347,240 | B1 | 2/2002 | Foley et al. | EP | 0 062 941 | 3/1982 |
| 6,351,659 | B1 | 2/2002 | Vilsmeier | EP | 0 119 660 | 9/1984 |
| 6,370,411 | B1 | 4/2002 | Osadchy et al. | EP | 0 155 857 | 1/1985 |
| 6,381,485 | B1 | 4/2002 | Hunter et al. | EP | 0 319 844 A1 | 1/1988 |
| 6,424,856 | B1 | 7/2002 | Vilsmeier et al. | EP | 0 326 768 | 12/1988 |
| 6,427,314 | B1 | 8/2002 | Acker | EP | 0419729 A1 | 9/1989 |
| 6,428,547 | B1 | 8/2002 | Vilsmeier et al. | EP | 0350996 A1 | 1/1990 |
| 6,434,415 | B1 | 8/2002 | Foley et al. | EP | 0 651 968 A1 | 8/1990 |
| 6,437,567 | B1 | 8/2002 | Schenck et al. | EP | 0 427 358 | 10/1990 |
| 6,445,943 | B1 | 9/2002 | Ferre et al. | EP | 0 456 103 | 5/1991 |
| 6,447,488 | B2 | 9/2002 | Estabrook et al. | EP | 0 581 704 B1 | 7/1993 |
| 6,468,265 | B1 * | 10/2002 | Evans et al. ........................ 606/1 | EP | 0 655 138 B1 | 8/1993 |
| 6,470,207 | B1 | 10/2002 | Simon et al. | EP | 0 894 473 A2 | 1/1995 |
| 6,474,341 | B1 | 11/2002 | Hunter et al. | EP | 0 908 146 | 10/1998 |
| 6,478,802 | B2 | 11/2002 | Kienzle, III et al. | EP | 0 930 046 | 10/1998 |
| 6,484,049 | B1 | 11/2002 | Seeley et al. | EP | 1523951 | 4/2005 |
| 6,490,475 | B1 | 12/2002 | Seeley et al. | FR | 2417970 | 2/1979 |
| 6,493,573 | B1 | 12/2002 | Martinelli et al. | GB | 2 094 590 | 2/1982 |
| 6,498,944 | B1 * | 12/2002 | Ben-Haim et al. ............ 600/407 | GB | 2 164 856 | 10/1984 |
| 6,499,488 | B1 | 12/2002 | Hunter et al. | JP | 61-94639 | 10/1984 |
| 6,516,046 | B1 | 2/2003 | Fröhlich et al. | JP | 62-327 | 6/1985 |
| 6,527,443 | B1 | 3/2003 | Vilsmeier et al. | JP | 63-240851 | 3/1987 |
| 6,551,325 | B2 | 4/2003 | Neubauer et al. | JP | 3-267054 | 3/1990 |
| 6,572,624 | B2 | 6/2003 | U et al. | JP | 2765738 | 4/1998 |
| 6,584,174 | B2 | 6/2003 | Schubert et al. | WO | 2 618 211 | 7/1987 |
| 6,609,022 | B2 | 8/2003 | Vilsmeier et al. | WO | WO 88/09151 | 12/1988 |
| 6,611,700 | B1 | 8/2003 | Vilsmeier et al. | WO | WO 89/05123 | 6/1989 |
| 6,640,128 | B2 | 10/2003 | Vilsmeier et al. | WO | WO 90/05494 | 11/1989 |
| 6,694,162 | B2 | 2/2004 | Hartlep | WO | WO 91/03982 | 4/1991 |
| 6,701,179 | B1 | 3/2004 | Martinelli et al. | WO | WO 91/04711 | 4/1991 |
| 6,796,963 | B2 | 9/2004 | Carpenter et al. | WO | WO 91/07726 | 5/1991 |
| 7,366,562 | B2 | 4/2008 | Dukesherer et al. | WO | WO 92/03090 | 3/1992 |
| 2001/0007918 | A1 | 7/2001 | Vilsmeier et al. | WO | WO 92/06645 | 4/1992 |
| 2001/0044578 | A1 | 11/2001 | Ben-Haim et al. | WO | WO 94/04938 | 3/1994 |
| 2002/0087101 | A1 | 7/2002 | Barrick et al. | WO | WO 95/07055 | 9/1994 |
| 2002/0095081 | A1 | 7/2002 | Vilsmeier | WO | WO 94/23647 | 10/1994 |
| 2002/0147497 | A1 | 10/2002 | Belef et al. | WO | WO 94/24933 | 11/1994 |
| 2003/0009169 | A1 | 1/2003 | Young et al. | WO | WO 96/32059 | 11/1995 |
| 2003/0066538 | A1 | 4/2003 | Martinelli et al. | WO | WO 96/11624 | 4/1996 |
| 2003/0078003 | A1 | 4/2003 | Hunter et al. | WO | WO-9632060 | 10/1996 |
| 2003/0097061 | A1 | 5/2003 | Ferre et al. | WO | WO 97/49453 | 6/1997 |
| 2003/0114778 | A1 | 6/2003 | Vilsmeier et al. | WO | WO-9729710 | 8/1997 |
| 2003/0184285 | A1 | 10/2003 | Anderson et al. | WO | WO 97/36192 | 10/1997 |

| | | |
|---|---|---|
| WO | WO 99/23956 | 11/1997 |
| WO | WO 98/08554 | 3/1998 |
| WO | WO 98/38908 | 9/1998 |
| WO | WO 99/15097 | 9/1998 |
| WO | WO 99/21498 | 10/1998 |
| WO | WO 99/27839 | 12/1998 |
| WO | WO 99/33406 | 12/1998 |
| WO | WO 99/38449 | 1/1999 |
| WO | WO 99/52094 | 4/1999 |
| WO | WO 99/26549 | 6/1999 |
| WO | WO 99/29253 | 6/1999 |
| WO | WO 99/37208 | 7/1999 |
| WO | WO 99/60939 | 12/1999 |
| WO | WO 01/30437 A1 | 5/2001 |
| WO | WO-0130257 | 5/2001 |

OTHER PUBLICATIONS

Bergstrom et al. Stereotaxic Computed Tomography, Am. J. Roentgenol, vol. 127 pp. 167-170 (1976).

Brown, R., M.D., A Stereotactic Head Frame for Use with CT Body Scanners, Investigative Radiology @ J.B. Lippincott Company, pp. 300-304 (Jul.-Aug. 1979).

Bucholz, R.D., et al. Image-guided surgical techniques for infections and trauma of the central nervous system, Neurosurg. Clinics of N. A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).

Cutting M.D. et al., Optical Tracking of Bone Fragments During Craniofacial Surgery, Second Annual International Symposium on Medical Robotics and Computer Assisted Surgery, pp. 221-225, (Nov. 1995).

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., Jr. et al, Optical localization for interactive, image-guided neurosurgery, SPIE, vol. 2164, pp. 137-145 (undated).

Galloway, R.L., et al., Interactive Image-Guided Neurosurgery, IEEE Trans. on Biomed. Eng., vol. 89, No. 12, pp. 1226-1231 (1992).

Gomez, C.R., et al., Transcranial Doppler Ultrasound Following Closed Head Injury: Vasospasm or Vasoparalysis?, Surg. Neurol., vol. 35, pp. 30-35 (1991).

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).

Guthrie, B.L., Graphic-Interactive Cranial Surgery: The Operating Arm System, Handbook of Stereotaxy Using the CRW Apparatus, Chapter 13, pp. 193-211 (undated.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Computer-Directed Stereotactic Resection of Brain Tumors, Neurologica Operative Atlas, vol. 1, No. 4, pp. 299-313 (1991).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Ng, W.S. et al., Robotic Surgery—A First-Hand Experience in Transurethral Resection of the Prostate Surgery, IEEE Eng. in Med. and Biology, pp. 120-125 (Mar. 1993).

Penn, R.D., et al., Stereotactic Surgery with Image Processing of Computerized Tomographic Scans, Neurosurgery, vol. 3, No. 2, pp. 157-163 (Sep.-Oct. 1978).

Pixsys, 3-D Digitizing Accessories, by Pixsys (marketing brochure)(undated) (2 pages).

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäßmißbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341 (undated).

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurg, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

"Prestige Cervical Disc System Surgical Technique" Brochure, 12 pgs.

Adams et al., "Orientation Aid for Head and Neck Surgeons," Innov. Tech. Biol. Med., vol. 13, No. 4, 1992, pp. 409-424.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel, Edmund C. et al., "Magnetic Source Imaging: a Review of the Magnes System of Biomagnetic Technologies Incorporated," Neurosurgery, vol. 33, No. 2 (Aug. 1993), pp. 252-259.

Bouazza-Marouf et al.; "Robotic-Assisted Internal Fixation of Femoral Fractures", IMECHE., pp. 51-58 (1995).

Brack, C. et al., "Accurate X-ray Based Navigation in Computer-Assisted Orthopedic Surgery," CAR '98, pp. 716-722.

Bryan, "Bryan Cervical Disc System Single Level Surgical Technique", Spinal Dynamics Brochure, 2002, pp. 1-33 (described by Vincent Bryan).

Bucholz, Richard D. et al., "Variables affecting the accuracy of stereotactic localization using computerized tomography," Journal of Neurosurgery, vol. 79, Nov. 1993, pp. 667-673.

Champleboux et al., "Accurate Calibration of Cameras and Range Imaging Sensors: the NPBS Method," IEEE International Conference on Robotics and Automation, Nice, France, May 1992.

Champleboux, Guilleme "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Gildenberg et al., "Calculation of Stereotactic Coordinates from the Computed Tomographic Scan," Neurosurgery, vol. 10, No. 5, May 1982, pp. 580-586.

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. 1996, pp. 42-51.

Gueziec et al., "Registration of Computed Tomography Data to a Surgical Robot Using Fluoroscopy: A Feasibility Study," Computer Science/Mathematics, Sep. 27, 1996, 6 pages.

Hamadeh et al, "Kinematic Study of Lumbar Spine Using Functional Radiographies and 3D/2D Registration," TIMC UMR 5525—IMAG, 1997.

Hamadeh et al., "Automated 3-Dimensional Computed Tomographic and Fluoroscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hatch, et al. "Reference-Display System for the Integration of CT Scanning and the Operating Microscope," Thesis, Thayer School of Engineering, Oct. 1984, pp. 1-189.

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique for Accurate Transpedicular Screw Fixation Using CT Data and a 3-D Optical Localizer," TIMC, Faculte de Medecine de Grenoble.

Lavallee et al., "Image guided operating robot: a clinical application in stereotactic neurosurgery," Proceedings of the 1992 IEEE International Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Lavallee, "VI Adaption de la Methodologie a Quelques Applications Cliniques," Chapitre-VI, pp. 133-148.

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrate Assistee par Ordinateur: Appication au Vissage Pediculaire, Innov. Tech. Biol. Med., vol. 11, No. 5, 1990, pp. 559-566.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Phillips et al., "Image Guided Orthopaedic Surgery Design and Analysis," Trans Inst. MC, vol. 17, No. 5, 1995, pp. 251-264.

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Smith et al., "Computer Methods for Improved Diagnostic Image Display Applied to Stereotactic Neurosurgery," Automedical, vol. 14, 1992, pp. 371-382.

Viant et al., "A Computer Assisted Orthopaedic System for Distal Locking of Intramedullary Nails," Proc. of MediMEC '95, Bristol, 1995, pp. 86-91.

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Weese et al., "An Approach to 2D/3D Registration of a Vertebra in 2D X-ray Fluoroscopies with 3D CT Images," pp. 119-128.

Germano, "Instrumentation, Technique, and Technology", Neurosurgery, vol. 37, No. 2, Aug. 1995, pp. 348-350.

Merloz, et al., "Computer Assisted Spine Surgery", Clinical Assisted Spine Surgery, No. 337, pp. 86-96.

Hatch, et al., "Reference-Display System for the Integration of CT Scanning and the Operating Microscope", Proceedings of the Eleventh Annual Northeast Bioengineering Conference, May 1985, pp. 252-254.

Laitinen, Lauri V., "Noninvasive multipurpose stereoadapter," Neurological Research, Jun. 1987, pp. 137-141.

Kelly, Patrick J., et al., "Computer-assisster stereotaxic laser resection of intra-axial brain neoplasms," J. Neurosurg., vol. 64, Mar. 1986, pp. 427-439.

Laitinen, Lauri V. et al., "An Adapter for Computed Tomography-Guide Stereotaxis," Surg. Neurol., 1985, pp. 559-566.

Homer, Neil, et al., "A Comparison of CT-Stereotaxic Brain Biopsy Techniques," Investigative Radiology, Sep.-Oct. 1984, pp. 367-373.

Heilbrun, Peter M., et al., "Preliminary experience with Brown-Roberts-Wells (BRW) computerized tomography stereotaxic guidance system," J. Neurosurg., vol. 59, Aug. 1983, pp. 217-222.

Leksell, L., et al., "Stereotaxis and Tomography a Technical Note," 1980, Acta Neurochururgica 52, pp. 1-7.

The Laitinen Stereotactic System, E-2-E6.

Bucholz, Richard D., et al., "Variables affecting the accuracy of stereotactic localization using computerized tomography," J. Neurosurg., vol. 79, Nov. 1993, pp. 667-673.

Foley, Kevin T., "The StealthStation™; Three Dimensional Image-Interactive Guidance for the Spine Surgeon," Spinal Frontiers, Apr. 1996, pp. 7-9.

Barrick, E. Frederick, et al., "Technical Difficulties with the Brooker-Wills Nail in Acute Fractures of the Femur," J. Orthopaedic Trauma, vol. 4, 1990, pp. 144-150.

Barrick, E. Frederick, et al., "Distal Locking Screw Insertion Using a Cannulated Drill Bit: Technical News," J. Orthopaedic Trauma, vol. 7, 1993, pp. 248-251.

Smith, Kurt R., et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

International Search Report mailed Feb. 26, 2001 for PCT/US00/29880.

Written Opinion mailed Aug. 14, 2001 for PCT/US00/29880.

International Preliminary Examination Report for PCT/US00/29880.

German Office Action mailed Jan. 5, 2009 for German Publication No. 100851371 claiming benefit of PCT/US00/29880, filed Oct. 27, 2000; which claims priority of U.S. Appl. No. 09/428,721, filed Oct. 28, 1999.

"AxiEM Electromagetic Navigation," tri-fold brochure, Medtronic Navigation (2005) 2 pages.

European Search Report completed Jul. 6, 2005 for European Application No. EP 04 02 4680 claiming benefit of U.S. Appl. No. 10/688,068, filed Oct. 17, 2003 and U.S. Appl. No. 10/941,782, filed Sep. 15, 2004.

European Search Report mailed Nov. 29, 2010 for European Application No. EP10183187 claiming benefit of EP 040246803, filed Oct. 15, 2004; which claims benefit of U.S. Appl. No. 10/941,782, filed Sep. 15, 2004; which claims benefit of U.S. Appl. No. 10/688,068, file Oct. 17, 2003.

European Search Report mailed Nov. 29, 2010 for European Application No. EP10183240 claiming benefit of EPSN 04024680.3, filed Oct. 15, 2004; which claims benefit of U.S. Appl. No. 10/941,782, filed Sep. 15, 2004; which claims benefit of U.S. Appl. No. 10/688,068, filed Oct. 17, 2003.

Medtronic Navigation, "StealthStation® AXIEM™ Electromagnetic Navigation . . . ", 2005, wvvw.stealthstation.com/physician/spine/library/axiem_ent.jsp, printed Aug. 19, 2006 (2 pages).

Partial European Search Report completed Mar. 16, 2005 for European Application No. EP 04 02 4680 claiming benefit of U.S. Appl. No. 10/688,068, filed Oct. 17, 2003 and U.S. Appl. No. 10/941,782, filed Sep. 15, 2004.

Partial European Search Report completed Nov. 26, 2007 for European Application No. EP 06 11 6892 claiming benefit of U.S. Appl. No. 11/179,044, filed Jul. 11, 2005.

Partial European Search Report completed Nov. 8, 2006 for European Application No. EP 06 11 6892 claiming benefit of U.S. Appl. No. 11/179,044, filed Jul. 11, 2005.

* cited by examiner

SURGICAL SENSOR

CROSS-REFERENCE TO RELATED APPLICATIONS

This application is a continuation of U.S. patent application Ser. No. 10/289,869 filed on Nov. 7, 2002, which is a continuation of U.S. patent application Ser. No. 09/428,721, filed on Oct. 28, 1999, now U.S. Pat. No. 6,499,488. The disclosures of the above applications are incorporated herein by reference.

FIELD

The present teachings relate to a surgical sensor which may be integrated with an anatomical anchor. The sensor has particular applicability in surgical procedures where it is desirable to track the relative movement of one or more structures.

BACKGROUND

Many surgical procedures are planned and guided using images obtained from imaging systems such as magnetic resonance imagers (MRIs), computer tomographic imagers (CTs), x-ray imagers, positron emission tomographic (PET) scanners, and photo-emission computer technology (SPECT). These systems permit physicians to obtain detailed preoperative (or intraoperative) views of anatomical structures using noninvasive procedures. Once these images are obtained, the physician typically uses the images to plan a corrective surgical procedure. With the patient lying on an operating table, the images may be "registered" with the corresponding physical space of the patient, and displayed on a screen in the operating room (OR). As the physician navigates probes or other medical instruments within the patient, sensors on the instruments relay positional information to a computer. The computer, in turn, overlays a display of the position of the instrument on the image of the anatomical structure. In this way, the physician may navigate through a surgical procedure by viewing a display screen in the OR. An example of a related art system is found in U.S. patent application Ser. No. 08/809,404, now U.S. Pat. No. 6,236,875, entitled: "Surgical Navigation System Including Reference and Localization Frame," and which is fully incorporated herein by reference.

Until now, the tracking of anatomical structures has been largely limited to external tracking, either by taping a sensor to a patient's skin, or by affixing an external clamp to the patient, such as a Mayfield clamp, attached externally to a patient's head.

U.S. patent application Ser. No. 08/931,654, now U.S. Pat. No. 6,347,240, entitled "Bone Navigation System" which is incorporated fully herein by reference discloses a system which employs screws extending from a bone fragment through a patient's skin and connected to a platform external to the patient. Tracking elements such as, for example, emitters are located on the platform so that when a bone fragment moves, so too does the platform with the connected tracking elements. An array in the OR tracks movement of the tracking elements, and this movement is correlated to the movement of the bone fragment, in order to precisely track the movement of the bone fragment. Alternatively, clamps may be used, in place of screws, to secure an array of tracking elements to a bone structure. While such related art systems may generally be reliable, their structure is somewhat cumbersome, especially when the movement of multiple anatomical structures needs to be tracked. In addition, the use of the tracking elements and receiving array requires an unobstructed line of sight therebetween which not only limits implantation within a patient, but also can lead to interference.

For these reasons, in procedures such as those involving the spine or the reconstruction or repair of vertebral bodies, fractured skulls, fragmented bones, or other damaged boney structures, it has been somewhat difficult to track the relative movement of multiple anatomical structures.

SUMMARY

Enabling the detection of anatomical structure movement during medical procedures without the use of cumbersome external equipment fixed to the patient.

To provide a localization system for internal and/or external anatomical structures that do not require an unobstructed line of sight between a positional sensor and a detector.

To provide a localization system for internal anatomical structures which may be employed with minimal invasive procedures.

To provide an integrated anchor and localization sensor that may be deployed with relative ease.

To provide an anatomical anchor which may serve as both a preprocedural and intraprocedural fiducial marker.

To provide a reliable localization marker which may be placed in a patient in advance of a procedure and which may remain in the patient for a period of time following the procedure.

To enable movement detection, with five or six degrees of freedom, of an anatomical structure or surgical instrument (whether the instrument be an anchor, a catheter, or any other medical instrument).

The teachings, in their broadest sense, may comprise one or more of the following aspects, either alone or in combination with one or more additional elements:

an anatomical anchor/sensor, a receiver on an anchor for sensing signals generated external to the anchor, a transmitter on an anchor for conveying signals indicative of the anchor's location, a signal generator on an anchor, a connection for securing a receiver to an anatomical anchor, a receiver and/or transmitter on a surgical screw, staple, pin rod, needle or soft tissue anchor, an electromagnetic sensing coil on an anchor, a magnet on an anchor, an electromagnetic sensor having multiple collinear coils wound at differing angles, whether disposed on an anchor, a catheter, or other medical instrument, hard-wiring a transmitter on an anchor to a processor, affixing a wireless transmitter to an anchor, affixing a conductive electrode to an anatomical anchor, a surgical screw having a hollow containing a sensor, affixing a sensor to anchor using potting material, a sensor housing for the head of a screw, an attachable/detachable sensor mount for an anchor, a grasping region for permitting medical personnel to screw a portion of a screw/sensor into an anatomical structure, an integrated anatomical anchor/sensor where the sensor is detachable, methods and apparatuses for deploying an integrated anchor/sensor, methods for making and using the above items, procedures where the relative movement of instruments and/or anatomical structures are tracked and displayed, and any other novel and unobvious aspects of the following disclosure and/or claims.

BRIEF DESCRIPTION OF THE DRAWINGS

The present teachings will become more fully understood from the detailed description and the accompanying drawings, wherein.

DETAILED DESCRIPTION OF VARIOUS EMBODIMENTS

The following description of various embodiments is merely exemplary in nature and is in no way intended to limit the present teachings, its application, or uses.

The teachings will now be described in connection with the Figures wherein like parts are numbered with the same reference numerals for ease of discussion.

Figures 1A, 1B:
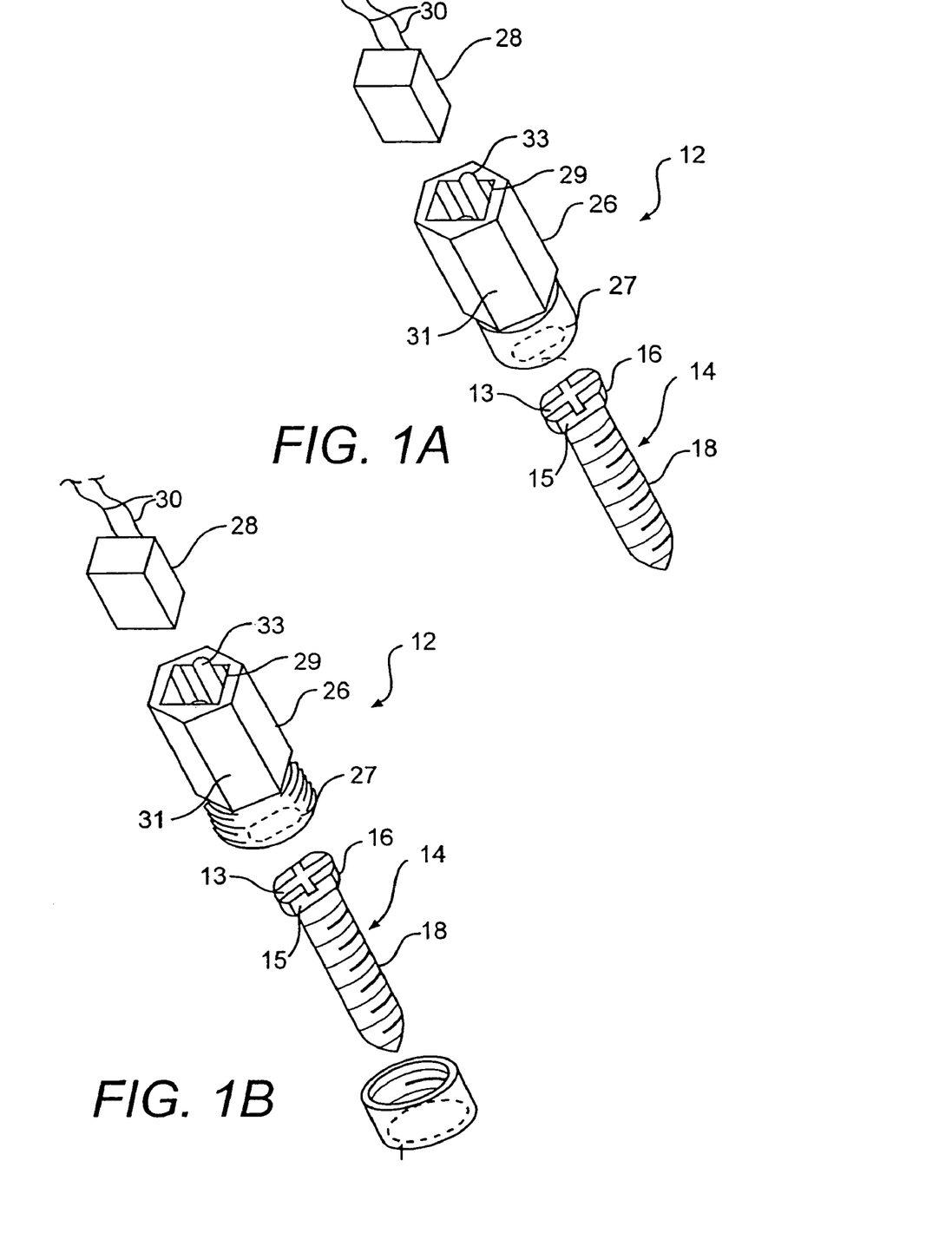
FIG. 1A is an exploded view of an integrated sensor and bone screw in accordance with one embodiment of the present invention.
FIG. 1B is an exploded view of an integrated sensor and bone screw in accordance with another embodiment of the present invention.

In accordance with the teachings, there is provided an integrated surgical anchor/localization sensor. An example of such an integrated unit is designated by reference number 12 in FIG. 1.

According to the invention, the anchor is configured to be secured to an anatomical structure. As illustrated in FIG. 1, an anchor in accordance with the invention may, by way of example, include a surgical screw 14. Screw 14 has a head portion 16, and a threaded portion 18. The threaded portion 18 is configured to be secured into boney structure such as portions of long bones, vertebral bodies, the skull, or any other boney anatomical structure. In an preferred embodiment, the anchor may be a 2.2 mm cross-drive screw, 3-7 mm in length. Preferably, the screw has keyed head portions 15 so that a connector may be securely fastened to it. Screw 15 may also contain slots 13 enabling the screw to be driven by various convention surgical screw drivers. It is also preferable for the screw 14 to be constructed of a material that will appear on an image scan and that will not cause interference with the surgical guidance system in which it is intended to be used. If an anchor is scanably detectable, it may alternatively be used as a fiducial marker. By way of example, when used with electromagnetic guidance systems, the screw may be constructed of aluminum.

While aspects of the invention are described herein in connection with surgical screws, the invention in its broadest sense is not so limited. Other anchors may be used in connection with the invention. By way of example only, such other anchors may include surgical staples, pins, rods, soft tissue anchors such as pigtails, and headframe (e.g., Mayfield) pins.

Figure 2A:
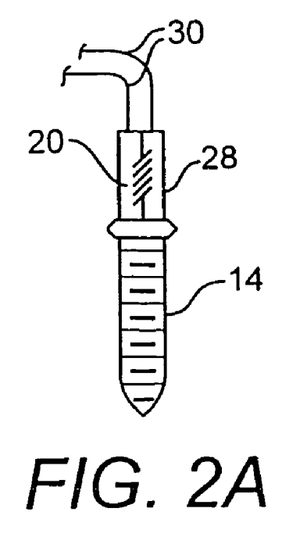
FIG. 2A is a schematic diagram of a single coil sensor in accordance with the invention.
Figure 2B:
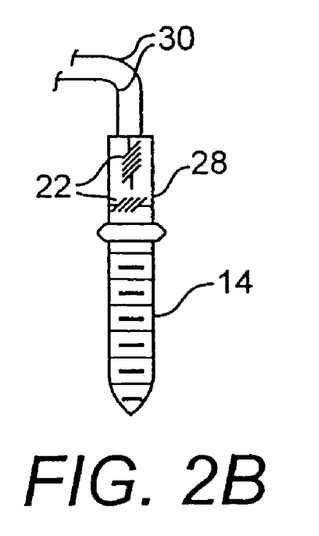
FIG. 2B is a schematic diagram of a dual-orthogonal coil sensor in accordance with the invention.
Figure 2C:
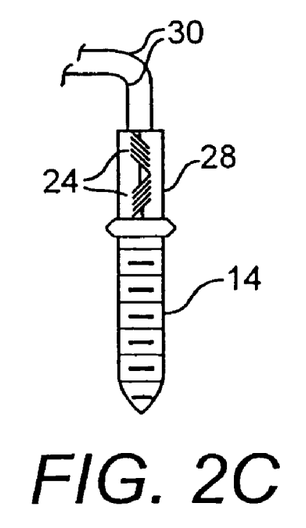
FIG. 2C is a schematic diagram of a dual-coaxial coil sensor in accordance with the invention.
Figure 3:
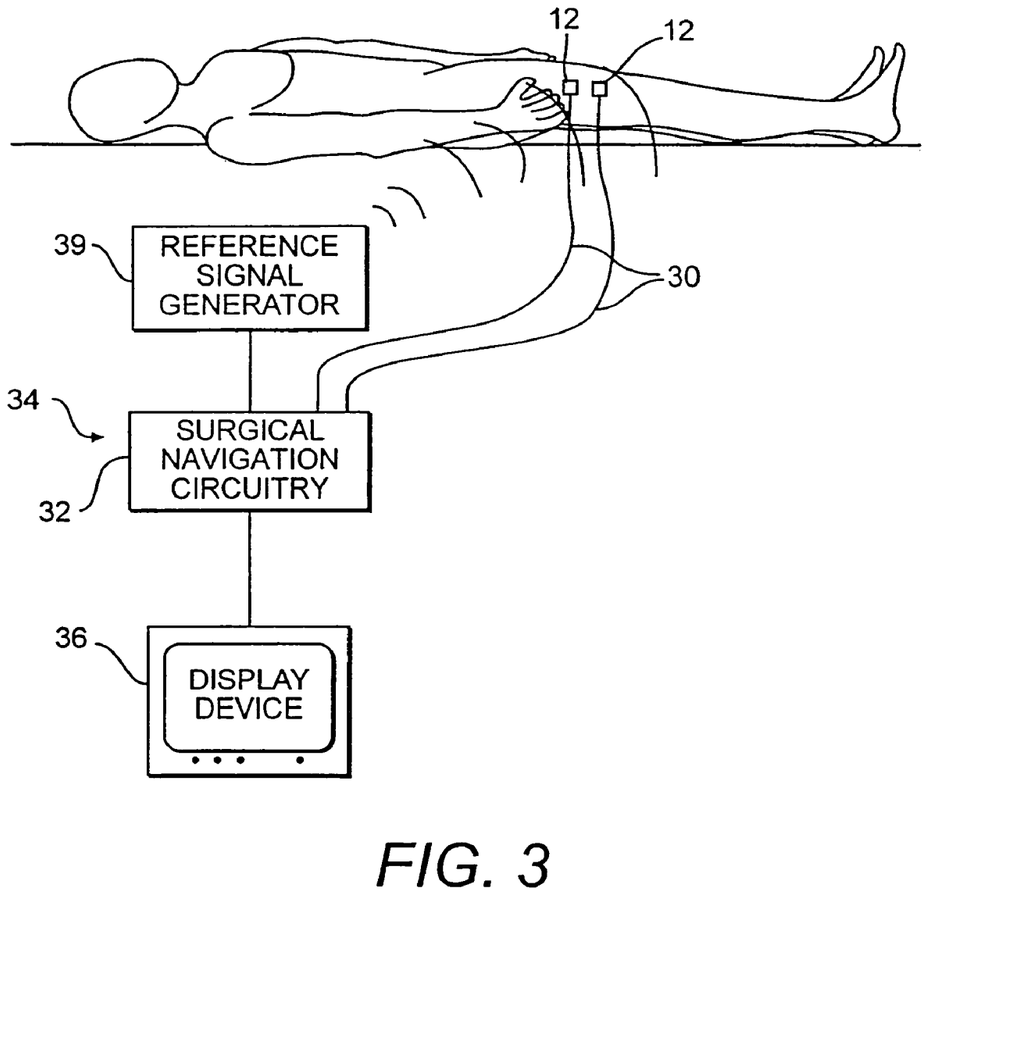
FIG. 3 is a schematic diagram of a preferred system of the invention and the environment of its use.

In accordance with the invention, there is also provided a receiver for sensing reference signals generated by a surgical guidance system. Such a system typically includes a reference signal generator 39 as schematically depicted in FIG. 3. When an electromagnetic guidance system is to be used in connection with the invention, the receiver may include at least one electromagnetic sensor 28 as schematically depicted in FIGS. 2A-2C. The invention is not limited to any specific localization guidance system or algorithm. Nevertheless, an example of an acceptable system and algorithm may be found in U.S. Pat. No. 5,592,939, entitled: "Method and System for Navigating a Catheter Probe," and which is fully incorporated herein by reference.

FIG. 2A illustrates a sensor 28 having a single coil 20. Depending on the specifics of the guidance system employed, such a sensor is typically capable of detecting position with either three or five degrees of freedom. In contrast, FIGS. 2B and 2C illustrate sensors 28 having multiple coils capable of detecting position with up to six degrees of freedom. More particularly, the coil arrangement illustrated in FIG. 2B enables a reference signal to be detected with two orthogonal sensing coils 22. Alternatively, a plurality of collinear coils may be employed. For example, in the coaxial arrangement illustrated in FIG. 2C, two collinear sensing coils 24 are wound at differing or opposing angles. While any opposing angles will work, a preferred angle is 90°. In this manner, each coil will provide unique feedback in response to the same reference signal generated by an electromagnetic guidance system.

The coil arrangement of FIG. 2C also has applicability in connection with medical devices other than anchors. For example, the collinear nature of the arrangement makes it particularly suitable for devices that have working channels such as catheters where coils of differing angles may be wrapped around the working channel to thereby minimize the size of the device.

The coil(s) of sensor 28 may be constructed of 40 AWG wire wrapped approximately 200 turns. Alternatively, the sensors may be 10 µH-1000 µH surface-mounted inductors, preferably non-shielded. In an alternative embodiment, a conductive localization system may be employed. In this situation, sensor 28 may include a conductive electrode receiver. While the preferred electromagnetic system is disclosed as including coil sensor, any electromagnetic sensor may be used including, but not limited to flux gates and reed switches.

The invention may also include a transmitter for conveying to a processor signals received by the receiver. In a preferred embodiment, the transmitter may simply include two wires 30 for hardwiring the sensor 28 to the electronics 32 of a surgical guidance system 34 (schematically illustrated in FIG. 3). The transmitter wires 30 may have, at their distal ends (not shown) connectors for selectively connecting them to the surgical guidance system 34. Preferably, the transmitter wires 30 include two pair of 40 AWG twisted bifilar wire, with an outside diameter less than about 0.062 inches. It is also preferable that the transmitter wires be compatible with sterilization processes so that they may be safely used within an anatomical body.

In an alternative embodiment, the transmitter may be wireless, transmitting signals to the surgical guidance system via radio frequency, for example. In such an embodiment, a transmitting circuit and antenna may also be part of sensor 28. Since the details of wireless transmitter systems are known in the art, for brevity, they are not repeated herein. Sensor 28 may further include a battery (not shown) for powering the transmitter. Alternatively, a voltage may be provided to the transmitter by induction using an external coil included as part of sensor 28. Examples of such systems are described in U.S. patent application Ser. No. 09/428,722; now U.S. Pat. No. 6,474,341, entitled "Surgical Communication and Power System" which is fully incorporated herein by reference.

As previously described, a sensor located on an anchor may receive signals from a signal generator external to the patient. The invention may, however, be embodied in a system with the reverse arrangement—i.e., element 28 being a signal generator internal to the patient and the sensor being located external to the patient. In this scenario, and if the teachings according to various embodiments, uses an electromagnetic guidance system, the internal signal generator may, in its simplest form, be a magnet.

Also in accordance with the invention there may be provided a connector for securing the receiver to the anchor, the connector being configured so that the signals conveyed by the transmitter are indicative of a current position of the anchor. As embodied herein, and as illustrated in FIG. 1A, the connector may include housing 26 mounted to the head 16 of screw 14. Housing 26 may include wire relief groove 33 for transmitter wires 30. Housing 26 may also include a keyed opening 27 for receiving corresponding keyed screw head 16. This keyed arrangement prevents housing 26 from rotating on screw 14, thereby ensuring that the sensor 28 remains in a fixed position to provide an accurate reading of the position (i.e., location and/or orientation) of screw 14. Housing 26 preferably has a plurality of flat grasping surfaces 31 enabling the screw to be driven into a boney structure by manipulating the housing 26. Housing 26 may be either detachable, fixedly secured to, or integrally formed with screw 14, so long as it satisfies the function of securing a sensor to the screw. To this end, housing 26 may contain an opening 29 opposite keyed opening 27, for receiving sensor 28. If housing 26 is integrally formed with screw 14, slots 13 may be eliminated or alternatively located at the surface of opening 29.

FIG. 1B illustrates an arrangement similar to FIG. 1A, except that a threaded cap 17 screws onto threaded end 19 of housing 26, securing head 16 of screw 14 to housing 26. With this arrangement, sensor housing 26 may be selectively removed from screw 14.

Sensor 28 may be secured to housing 26 in any appropriate manner. For example, it may snap fit and/or be glued into opening 29. Alternatively, coils or other sensors may be deposited in opening 29 and the opening thereafter filled with a suitable potting material, such as surgical cement. In its broadest sense, the connector of the invention may be any material or mechanism capable of joining the receiver to the anchor, ranging form a quantity of potting material to structures which are molded, mechanically attached to, bonded to, or integrally formed with the anchor.

In an alternative embodiment (not shown) screw 14 may have a partially hollowed construction in lieu of the housing 26, and the receiver may be contained within the hollow. In such an embodiment, the connector may be potting material for securing the receiver within the hollow or may include a cartridge for removably securing the sensor in the hollow. In fact, removability of the sensor from the anchor may be beneficially incorporated into mechanical linkages to provide the physician with flexibility to attached and detach the sensor as the physician sees fit.

Figures 4A, 4B:
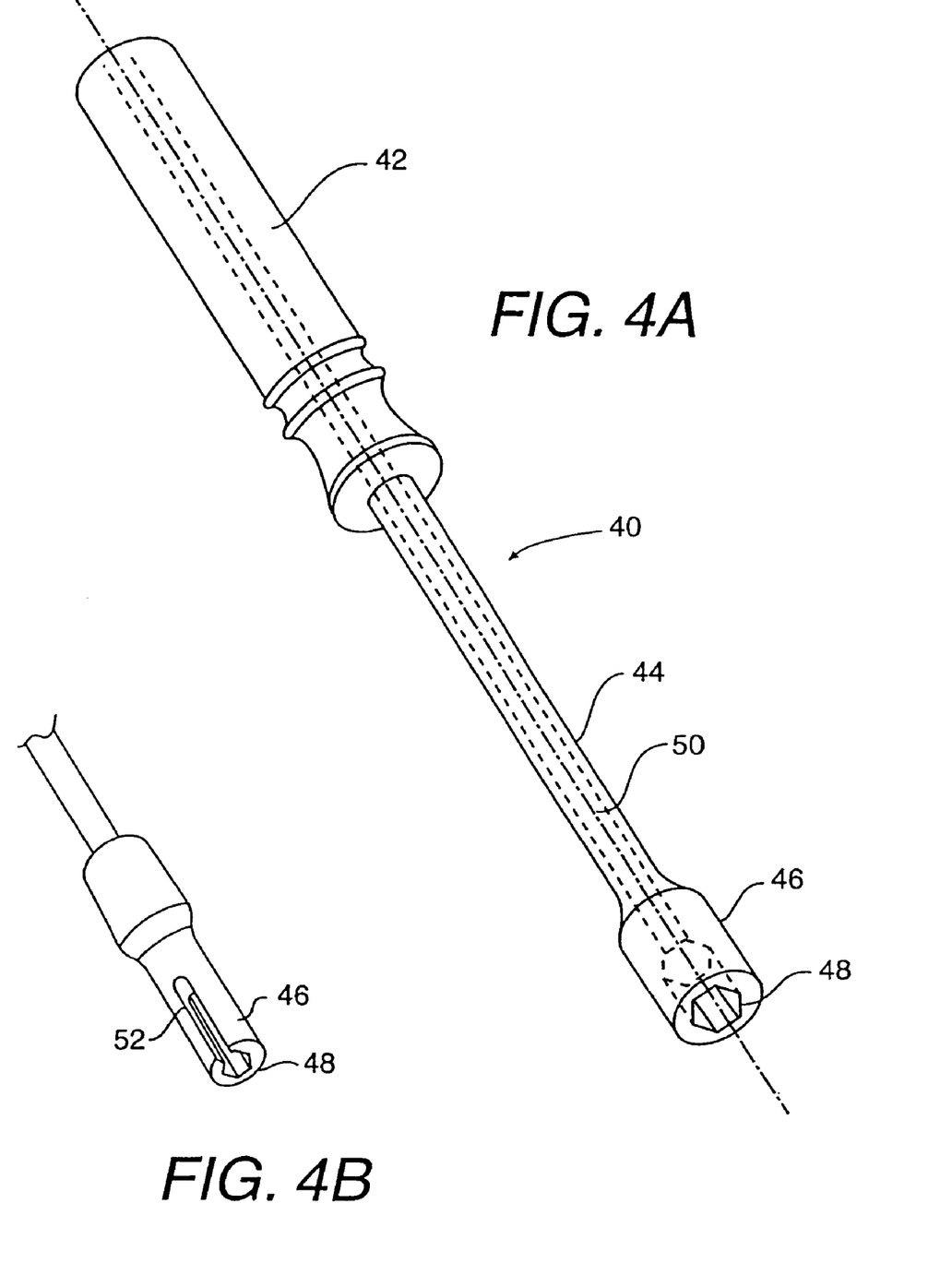
FIG. 4A is a perspective view of an embodiment of a driver associated with deploying the integrated sensors of FIGS. 1A and 1B.
FIG. 4B is a perspective of another embodiment of a driver associated with deploying the integrated sensors of FIGS. 1A and 1B.

While the anchor/sensor of the invention may be used as a fiducial marker, it has particular advantage for use in tracking boney anatomical structures such as vertebral bodies during spinal procedures or bone fragments during reconstructive procedures. By way of example, a physician may obtain an image of a fractured long bone using fluoroscopy or any other imaging device. Using a device such as cannulated driver 40 (illustrated in FIGS. 4A and 4B), the physician may implant screw/sensor into a boney structure. Specifically, driver 40 includes handle 42, neck 44, and socket 46. Socket 46 includes opening 48 shaped to engage grasping surfaces 31 of integrated screw/sensor 12. Driver 40 may include a cannula or opening 50 extending therethrough to accommodate transmitting wires 30. Alternatively, in lieu of opening 50, a slot 52 (FIG. 4B) in an edge of socket 46 may be provided to permit wires 30 to pass therethrough. In use, the physician loads a screw/sensor 12 into socket 48, and passes the loaded socket through an incision adjacent boney structure in which the screw is to be secured. Using handle 42, the physician turns the screw, securing it to the boney structure. Thereafter, the physician removes the driver 40, pulling it over the transmitting wires extended through opening 50 (FIG. 4A) or pulling the slot 52 (FIG. 46) away from wires 30.

After screwing an anchor/sensor 12 into each of the bone fragments, the sensors are then registered with the image, such as in a known manner. With the scanned image appearing on a display device 36, the physician may manipulate the fractured bone fragments, tracking their movement in real-time. This is achievable because the surgical navigation circuitry 32, receiving signals from anchor/sensors 12 in each fractured bone segment, can alter the image appearing on display 36 to reflect a current position of the bone segments. For example, the scanned image may be digitized and correlated to sensors 28 so that as the fractured portions of a bone are moved, simulated movement of those portions occur on display 36. In this way, a physician may precisely reset a fractured bone. Related procedures are disclosed in U.S. patent application Ser. No. 08/809,404, now U.S. Pat. No. 6,239,875, entitled "Surgical Navigation System Including Reference Frame and Localization Frame," and U.S. application Ser. No. 08/931,654, now U.S. Pat. No. 6,347,240, entitled "Bone Navigation System," both of which are fully incorporated herein by reference.

It will be apparent to those skilled in the art that various modifications and variations can be made to the structure and methodology of the present teachings without departing from the scope or spirit of the teachings. In view of the foregoing, it is intended that the present teachings cover modifications and variations of this teachings provided they fall within the scope of the following claims and their equivalents.

What is claimed is:

1. A method of determining a position of a plurality of portions of an anatomy, wherein the plurality of portions of the anatomy are naturally a single portion, comprising:
   attaching a first tracking sensor to a first portion of the anatomy including moving a first anchor into a first bone portion of the anatomy, interconnecting the first tracking sensor and the first anchor in a selected orientation, and fixing the first tracking sensor to the first anchor, wherein interconnecting the first tracking sensor and the first anchor in a selected orientation includes connecting the first tracking sensor to the first anchor in substantially only a single orientation determined by a first hollow formed relative to the first anchor;
   attaching a second tracking sensor to a second portion of the anatomy including moving a second anchor into a second bone portion of the anatomy; and
   moving the first portion of the anatomy relative to the second portion of the anatomy;
   wherein a selected position of the first portion and the second portion is determined at least in part with a first position signal produced from the first tracking sensor and a second position signal produced from the second tracking sensor.

2. The method of claim 1, wherein determining the selected position of the first portion, the second portion, or combinations thereof, include at least one of transmitting a signal, receiving a signal, or combinations thereof.

3. The method of claim 2, wherein determining the selected position of the first portion includes transmitting a first position signal from the tracking sensor and wherein determining the selected position of the second portion includes transmitting a second position signal from the second tracking sensor.

4. The method of claim 2, wherein determining the selected position of the first portion of the first tracking sensor includes:
producing a signal external to the anatomy;
receiving the signal produced external to the anatomy by said first tracking sensor; and
transmitting the first position signal from the first tracking sensor to a processor.

5. The method of claim 2, wherein determining the selected position of the second portion includes:
producing a signal external to the anatomy;
receiving the signal produced external to the anatomy by said second tracking sensor; and
transmitting the second position signal from the second tracking sensor to a processor.

6. The method of claim 1, further comprising:
positioning the first tracking sensor in the first hollow formed in the first anchor.

7. The method of claim 6, further comprising:
connecting the first tracking sensor with the first anchor;
wherein the first tracking sensor includes an electromagnetic sensor.

8. The method of claim 1, wherein the first bone portion and the second bone portion are anatomically a single bone.

9. The method of claim 8, further comprising:
manipulating the first portion of the anatomy and the second portion of the anatomy to achieve a selected anatomical orientation.

10. The method of claim 9, wherein manipulating the first portion of the anatomy and the second portion of the anatomy to achieve a selected anatomical orientation includes determining when the first portion of the anatomy and the second portion of the anatomy substantially mimic the natural anatomy.

11. The method of claim 1, further comprising:
transmitting at least one of the first position signal, the second position signal, or combinations thereof via radio frequencies.

12. The method of claim 1, further comprising:
providing a surgical instrument; and
providing a third tracking sensor with the surgical instrument.

13. The method of claim 12, further comprising:
providing a first portion of the third tracking sensor and a second portion of the third tracking sensor substantially collinear on the surgical instrument.

14. The method of claim 13, wherein the surgical instrument includes selecting at least one of a cannula, a probe, a catheter, or combinations thereof.

15. The method of claim 1, wherein attaching a second tracking sensor includes interconnecting a sensor element with a hollow portion of the second anchor interconnected with the second portion of the anatomy.

16. The method of claim 1, further comprising:
obtaining image data of the patient with an imaging system separate from the first anchor or the second anchor.

17. The method of claim 16, wherein obtaining image data includes obtaining image data of the patient with at least one of a magnetic resonance imager, a computer aided tomography imager, a fluoroscope, x-ray imagers, a positron emission scanner, a photon-emission computer tomography imager, or combinations thereof.

18. The method of claim 1, further comprising:
selecting a fractured anatomical portion that has at least a first fracture portion as the first bone portion and a second fracture portion as the second bone portion that have a naturally unfractured configuration;
wherein moving the first portion of the anatomy relative to the second portion of the anatomy is to substantially achieve the naturally unfractured configuration.

19. A method of determining a position of a plurality of portions of an anatomy, wherein the plurality of portions of the anatomy are naturally a single portion, comprising:
attaching a first tracking sensor to a first portion of the anatomy including moving a first anchor into a first bone portion of the anatomy, interconnecting the first tracking sensor and the first anchor in a selected orientation, and fixing the first tracking sensor to the first anchor;
attaching a second tracking sensor to a second portion of the anatomy including moving a second anchor into a second bone portion of the anatomy;
moving the first portion of the anatomy relative to the second portion of the anatomy;
determining a selected position of the first portion and the second portion of the anatomy at least in part with a first position signal produced from the first tracking sensor and a second position signal produced from the second tracking sensor;
registering the obtained image data to the physical space of the patient, wherein registering the image data includes matching a location of a fiducial in the physical space of the patient with an image space of the obtained image data;
anchoring at least one of the first tracking sensor, the second tracking sensor, or combinations thereof with the fiducial to the portion of the anatomy, wherein at least one of the first anchor or the second anchor is the fiducial;
displaying a movement of at least one of the first bone portion or the second bone portion of the anatomy with the obtained image data based on the registration of the obtained image data to the physical space; and
obtaining image data of the patient with an imaging system prior to attaching the first anchor or the second anchor.

20. A method of detecting and tracking a current position of a tissue of an anatomy, comprising:
attaching an anchor to the tissue;
imaging the anatomy after attaching the anchor to the anatomy to generate images;
attaching a tracking sensor to the anchor after the imaging of the anatomy;
registering the position of the anchor to the image data including image data of the anchor;
wherein a position of the surface of the anatomy is determined with a position signal produced by and conveyed from the tracking sensor; and
wherein the tracking sensor is configured so that the position signals correspond to the current position of the tissue;

wherein attaching a tracking sensor includes positioning the tracking sensor on an external portion of the anatomy.

21. The method of claim 20, wherein the position signal includes at least one of sensing a signal generated by a surgical navigation system, transmitting a signal from the tracking sensor to the surgical navigation system, or combinations thereof.

22. The method of claim 20, wherein the position signal of the tracking sensor is transmitted via radio frequencies.

23. The method of claim 20, wherein the tracking sensor attaches to the anchor in substantially only a single orientation.

24. The method of claim 20, further comprising:
transmitting a signal from a surgical navigation system to the tracking sensor; and
wherein producing a position signal includes sensing the signal from the surgical navigation system.

25. The method of claim 20, wherein attaching a tracking sensor includes:
attaching an anchor to the anatomy and providing a bore in the anchor; and
interconnecting the tracking sensor with the bore provided in the anchor.

26. The method of claim 20, further comprising:
providing a surgical instrument;
providing a surgical instrument sensor;
wherein said surgical sensor includes first sensing coil and a second sensing coil substantially collinear with the first sensing coil.

27. The method of claim 26, wherein the surgical instrument is selected from at least one of a probe, a cannula, a catheter, or combinations thereof.

28. The method of claim 20, further comprising:
displaying images of the anatomy on a display device;
manipulating the anatomy to move the anatomy, after registering the position of the anchor to the image data; and
viewing real time position of the anatomy based on the tracking sensor is configured so that the position signals correspond to the current position of the tissue.

29. The method of claim 28, wherein viewing real time position of the anatomy includes:
digitizing the generated images of the anatomy; and
illustrating movement of the digitized images in real-time based upon the real-time movement of the anatomy due at least to the registering the position of the anchor to the image data of the position of the anchor and the determining a position of the surface of the anatomy with the position signal.

* * * * *